United States Patent [19]

Meyers et al.

[11] Patent Number: 4,546,083

[45] Date of Patent: Oct. 8, 1985

[54] METHOD AND DEVICE FOR CELL CULTURE GROWTH

[75] Inventors: William E. Meyers, Helena; Lee R. Beck, Birmingham, both of Ala.

[73] Assignee: Stolle Research & Development Corporation, Cincinnati, Ohio

[21] Appl. No.: 487,824

[22] Filed: Apr. 22, 1983

[51] Int. Cl.[4] .......................... C12N 5/00; C12M 3/00
[52] U.S. Cl. .................................... 435/240; 435/284; 435/285
[58] Field of Search .............. 435/235, 240, 284, 285, 435/286, 287, 288, 813, 180, 181

[56] References Cited

U.S. PATENT DOCUMENTS

| | | | |
|---|---|---|---|
| 3,407,120 | 10/1968 | Weiss et al. | 435/240 X |
| 3,734,851 | 5/1973 | Matsumura | 210/632 |
| 3,997,396 | 12/1976 | Delente | 435/240 |
| 4,087,327 | 5/1978 | Feder et al. | 435/240 |
| 4,220,725 | 9/1980 | Knazek et al. | 435/285 |
| 4,252,653 | 2/1981 | Beck et al. | 210/446 X |
| 4,283,495 | 8/1981 | Lynn | 435/240 |
| 4,332,904 | 6/1982 | Kurane et al. | 435/813 X |
| 4,442,206 | 4/1984 | Michaels et al. | 435/284 X |

OTHER PUBLICATIONS

Carpenter, *Microbiology* (third edition), Philadelphia, W. B. Saunders, 1972, pp.354–355.
*Chemical Abstracts*, vol. 81, 1974, Abstract No. 167118d, Yavin et al. "Attachment and Culture of Dissociated Cells From Rat Embryo Cerebral Hemispheres on Polylysine-Coated Surface".
*Chemical Abstracts*, vol. 91, 1979, Abstract No. 87596z, Brodelius et al. "Immobilized Plant Cells for the Production and Transformation of Natural Products".

*Primary Examiner*—Robert J. Warden
*Assistant Examiner*—Randall E. Deck
*Attorney, Agent, or Firm*—Oblon, Fisher, Spivak, McClelland & Maier

[57] ABSTRACT

A cell culture device is disclosed for the cultivation of animal, plant, microbiological or artificial cells. The device involves a three-dimensional arrangement of fibers within a housing arranged to provide maximum exposed fiber surface flow channel diameter while also reducing the tortuosity of the flow path. Cells are bound to the fibers to allow them to contact nutrient fluid solution and thereby to remove any substances originating in said cells, such as viruses and pharmaceuticals.

20 Claims, 2 Drawing Figures

METHOD AND DEVICE FOR CELL CULTURE GROWTH

BACKGROUND OF THE INVENTION

1. Field of the Invention

The present invention relates to methods and devices used in the growth of cells in vitro, such as tissue culture growth.

2. Brief Description of the Prior Art

There has been in the last decade a dramatic increase in the knowledge and understanding of how best to exploit the ability of animal, plant or artificial cells (e.g., hybridomas) to obtain pharmacologically or diagnostically useful products.

For example, interferon is released by animal cells and inhibits viral infection. Its efficacy, however, is still not well established, principally because it has been hard to grow large quantities of the cells that produce it. Monoclonal antibodies are manufactured by hybridomas. Human monoclonal antibodies, produced by human hybridomas, can best be produced by growing the human hybridomas in culture. Urokinase, an enzyme that activates plasminogen to form the blood clot dissolving enzyme plasmin is obtained from kidney cells, preferably grown in culture. Human urokinase, the enzyme that activates plasminogen to form human plasmin can be obtained from human kidney cells, which are difficult to grow on a large scale.

The obvious promise of such cells as sources for products as those described, has motivated efforts to develop efficient large-scale cell culture systems. (See, for example, Feder and Tolbert, "The Large Scale Cultivation of Mammalian Cells", Scientific American, 248:36-43 (January, 1983)).

Generally, non-bacterial cells are fragile and complex. They are enclosed by a plasma membrane, and lack a cell wall. The nutritional requirements of animal and plant cells are quite stringent since, instead of being free-living organisms as bacteria, animal or plant cells are normally adapted to specialized life as part of an organized tissue. Their viability depends on the specialized function of many other cells and on a circulatory system that assures precisely adjusted and stable environments for each cell. Most cells, animal or plant, will not grow in suspension. They grow only when they attach themselves to a surface.

Over the years, techniques have been developed for growing cells on a small scale in the laboratory. A number of devices have been proposed for the cultivation of cells in vitro. See, for example, those described by Knazek et al., U.S. Pat. No. 4,184,922 or U.S. Pat. No. 4,220,725, Johnson et al., U.S. Pat. No. 4,317,886, Katinger et al., U.S. Pat. No. 4,259,449 or Baker et al., U.S. Pat. No. 4,321,330.

A need continues to exist for improved and efficient devices and methods for in vitro growing of cells from a variety of sources.

SUMMARY OF THE INVENTION

The present invention provides both a device and a method utilizing the device for the growth and cultivation of animal, plant or artificial cells.

The device utilized is an adaptation of the immuno hemoperfusion device described in U.S. Pat. No. 4,252,653 to Beck et al.. The device of Beck et al. in turn is a modification of a device described by Davis et al. (Transactions of the American Society for Artificial Internal Organs, 20:353). Davis et al. have described a hemoperfusion cartridge having carbon particles encapsulated within polymeric fibers which are deployed in a non-random fashion. Beck et al. modified this device to allow its application to highly specific alteration of biological fluid compositions. The fiber cartridge in Beck et al. '653, comprised a fixed non-random three-dimensional array of fibers whose chemical composition was such that additional chemical species could be grafted onto the surface or encapsulated within the matrix of the fibers. The additional species were fixed in such a manner that they might efficiently effect highly specific alterations upon biological fluids (e.g. blood) perfused through the cartridge.

The present invention discloses adaptations of the device of Davis et al. and Beck et al. for the growth of cells in culture. The invention also discloses generalized formulations and processes by which such cartridge devices may be manufactured, and describes methods and materials suitable for in vitro cell culture.

DETAILED DESCRIPTION OF THE PREFERRED EMBODIMENTS

The present invention comprises generally a fixed three-dimensional array of fibers contained within a housing, which provides for a continuous flow of nutrient fluid through the housing with maximum contact between fluid and fibers. The fibers are coated by covalent or noncovalent adsorptive attachment with any desired cells to be grown in culture. Therefore, the fibers are chosen so as to allow the desired cells to attach thereto and to contact nutrient components in the nutrient fluid, release toxic wastes thereinto, and not to lose their viability or metabolic efficiency.

The Device

Figure 1:
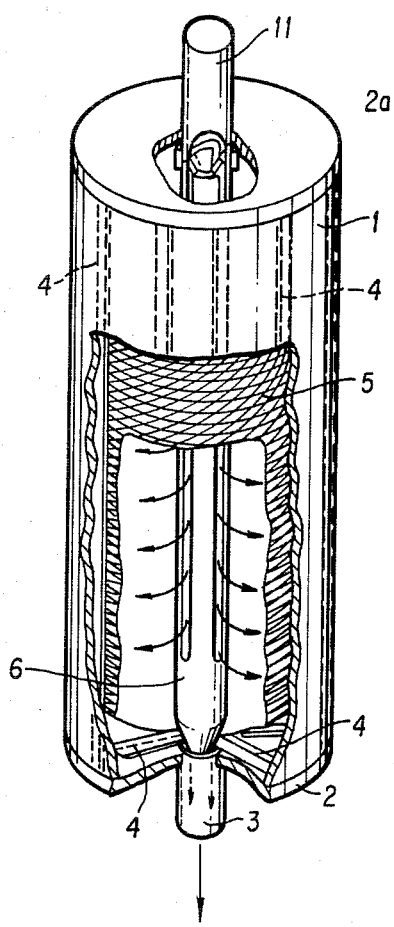
FIG. 1 is a cutaway perspective view of an assembled cell culture device.

The device shown in FIG. 1 is only an example of a possible device under this invention, and is not intended to limit the invention in any manner.

The assembled cartridge is composed of a glass or plastic jacket 1, capped at one end by a circular glass or plastic disc 2, and at its other end by a similar disc or spindle cap 2a. The disc 2 has, at its center, a cylindrical exit port 3. The jacket and cap have raised elements in the form of ribs 4 allowing for the unhindered axial flow of nutrient fluid along the surface of the jacket and cap, and allowing the exit thereof via the port. Within the jacket is a spool of fiber 5, helically wound about a glass or plastic spindle 6. The spindle and fiber fill the entire volume of the jacket with the exception of space between the ribs.

Another type of spindle can also be used. This spindle would be a simple hollow tube with holes along its length. The culture fluid can be pumped into the tube and exit at any point on its length. The hole size may be varied along the length to optimize the flow pattern.

Figure 2:
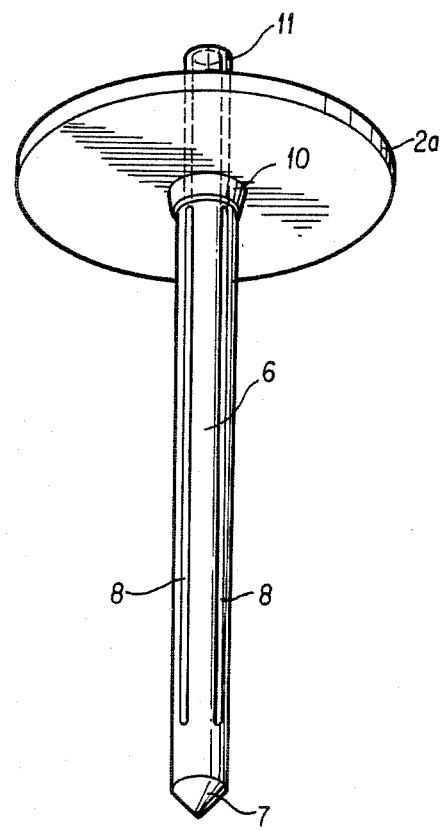
FIG. 2 is a perspective view of a spindle for the cartridge.

FIG. 2 shows the spindle 6, which is a glass or plastic rod which is conical at its base 7 and is slotted along its length as at 8. The rod is fitted at its top into a conical port 10, which is attached to the circular disk or spindle cap of like composition 2a. The diameter of the cap is chosen so that it makes a tight fit with a jacket and forms a sealed vessel when the spindle is inserted into the jacket. The external surface of the spindle cap has affixed to it a cylindrical entrance port 11 which is opposed to the conical port 10 and has an internal diameter which allows access of fluid passing through it to slots 8 of the spindle 6. Furthermore, the conical base of the spindle is of dimensions such that placement of the spindle base into the exit port results in contact of the spindle only with the ribs 4 of the jacket cap. This allows the nutrient fluids, which accumulate between the ribs, to exit through the lumen between the conical base 7 of the spindle 6 and the exit port 3. Thus, when the spindle is wound with a fiber, the flux of fluid entering through the device is that denoted by the arrows in FIG. 1.

Fiber Configuration and Housing

Fiber dimension and the specific three-dimensional array of fibers within the cartridge will determine the flow properties, available polymer surface area, and priming volume exhibited by the device. The last two conditions will be optimized when the fiber diameter is at the minimum value yielding sufficient strength and when the fiber array is chosen to yield a maximally compact bed. The flow properties will be effected in the opposite manner to that of available surface area and priming volume. These conditions must then be adjusted in order to optimize the overall efficiency with minimal damage to the culture cells.

The deployment of the fixed fiber array between the inlet and outlet of the cartridge jacket may be chosen from innumerable configurations. Among the more convenient configurations are the following:

(1) Deployment of fibers by winding about the outlet or inlet port. Such configurations may possess cylindrical symmetry about a tubular port having means for influx or efflux of fluid along the length of the tube. In another possible configuration of wound fibers, the fibers may be wound with spherical symmetry about a single central port;

(2) In cartridges wherein the fluid flows axially through the cartridge, the fibers may be deployed parallel to the direction of flow, being attached at each end of the cartridge. Another configuration employing an axial flow cartridge may have the fibers deployed transversely to the flow of fluid by attachment of the fibers to the lateral portions of the cartridge. A combination of parallel and transverse configuration may also be employed in which the fibers may be attached at both the ends and the lateral portions of the cartridge thus deployed in an interwoven fashion.

Fibers may be deployed as monofilaments or as multifilament yarns, and the device may contain one continuous fiber or numerous fibers. It is required only that the configuration of the cartridge housing and fiber deployment be consistent with fluid dynamics, compatible with minimal damage to the immobilized components on the device. These restrictions are well known to those skilled in the art.

Cells

Any cell, or combination of cells, capable of being cultured in vitro can be cultured in the device described in the present invention. Of particular interest are animal cells, plant cells, (e.g. human cells), microbiological cells (e.g., bacteria, yeasts) or artificial cells (e.g., hybridomas and genetically altered or otherwise modified cells). Also, micro-encapsulated cells with microcapsules bound to fibers can be used. For example, any of the cells described in the Description of the Prior Art can be immobilized on the device of the invention. The cells are broadly considered to be microfactories which elaborate and secrete any desired molecules or combinations of molecules such as enzymes, spore cells, pharmaceuticals, antibodies, virus, and the like.

Fibers

Generally, any fiber-forming material, either from natural or artificial origin, which is capable, by itself or through further treatment, of adsorbing viable cells on its surface, can be utilized. The material should be defined by several criteria: (1) It must be able to be formed into fibers strong enough for processing into a three-dimensional array; (2) The fibers must be essentially insoluble in a neutral aqueous solution; (3) The fibers may possess either a smooth, non-porous surface to decrease non-specific adsorption and entrapment, or a porous surface to increase surface area; (4) The fibers should release no toxic substances or fragments into the aqueous media percolating through them; (5) The degree of biocompatability of the fiber composition should be commensurate with the intended application. For long term applications the fiber should cause no irreversible cummulative deleterious alterations of the adsorbed cells; (6) The fibers employed must exhibit properties which will allow the attachment of cells thereon. Fibers thus may be chosen from one of the following categories: (A) substances of biological origin or products arising from them such as cellulose, perfluoroethylcellulose, cellulose triacetate, cellulose acetate, nitro cellulose, dextran, chitin, collagen, fibrin, elastin, keratin, cross-linked soluble proteins, polymerized soluble organic species of biological origin (polylactic acid, polylysine, nucleic acids), silk, rubber, starch, and hydroxyethyl starch; (B) heterochain synthetic polymers such as polyamides, polyesters, polyethers, polyurethanes, polycarbonates, and silicones; (C) hydrocarbon polymers such as polyethylene, polypropylene, polyisoprenes, polystyrenes, polyacrylics such as polyacrylamide, polymethacrylate, vinyl polymers such as a polyvinyl acetate, and halogenated hydrocarbon plastics such as PVC, polyfluorocarbons such as Teflon®, fluorocarbon copolymers and polychlorotrifluoroethylene; and (D) inorganic fibers such as fiber glass.

The fibers may be either solid or hollow in cross-section.

The fibers may be used as such or may be pretreated by physical or chemical methods to increase their adsorptivity towards cells. Chemical methods include treatment with anchoring groups such as fiber formation in the presence of polylysine, which covers the fibers with amino groups. Other techniques well known to those skilled in the art which have been utilized for the immobilization of cells, enzymes, solid phase immuno assays, enzyme linked immunosorbent assay, cell labelling and separation and hemodialysis can be utilized (see, for example, U.S. Pat. Nos. 4,031,201, 3,652,761, 4,059,685, 3,865,726, and Canadian Pat. No. 957,922).

Attachment of the cells to the fibers may be performed during polymer preparation, fiber spinning, just prior to placement of said fibers into the cartridge, or following the deployment of the fibers in the cartridge. The attachment should be permanent in the sense of being more than a mere temporary attachment as would be observed in using the device for removal of cells from blood in its known prior art immunohemoperfusion mode. By permanent is meant to imply that the attachment will be long enough to permit the collection of any desired metabolic product therefrom, e.g., one or more days.

Physical treatments of the fibers which surface-modify the same can be utilized. For example, glow discharge in a low pressure atmosphere of inert or reactive vapors is a technique which is preferred in the present invention, since it greatly increases the adsorptivity of cells thereon. Similarly, corona discharge at atmospheric pressures may be used. Chemical treatment of the fibers, such as coating with substances that promote cell attachment (e.g., collagen, poly-L-lysine, and the like), can also be used.

The cartridge system and device used in the present invention has many advantages over the use of flasks, roller bottles or beads, which are presently being used.

Surface area for cell binding is greatly increased. For example, in a cartridge 6 inches long and 3 inches in diameter, one can obtain about 1,000 square meters with polypropylene fibers, a substantial increase over such devices as culture flasks and roller bottles.

Although biobeads may have similar surface areas, the device of the invention has numerous advantages thereover. Nutrients can be fed into the cartridge of the invention so that all of the cells attached throughout the fiber bed can be supplied uniformly. The helical distribution of the fibers provides control over the packing volume of the fibers. It is thus possible to have variable open spaces within the cartridge; this variable can be adjusted depending on the loading and nature of desired nutrient feed rate. The flow system for the cartridge has the advantage that simple collection of product can be carried out. Fibers can be recycled by simply removing cells by trypsin hydrolysis or any other normally used methodology. The nutrient medium can be recirculated, it can be checked at outflow and any necessary salts, compositions or other culture requirements can be added thereto.

The system is reusable. It can be sterilized essentially like any other prior art culture device. This can be carried out by sterilization, autoclaving, ethylene oxide treatment, ethanol treatment and the like. The device can be built in a wide range of sizes, from a few milliliters to several gallons.

The cartridge-fiber combination has a non-abrasive configuration. Although with beads, one obtains good surface areas, there are several problems associated therewith. First, are the flow property problems of beads. If beads are used in a system which has been pressurized, one quickly obtains packing and poor flow. If one tries to use a fluidized bed system with beads, it is common to see bead-to-bead abrasion, which causes the cells to be released from the surface, and therefore result in substantial loss of materials. The fibers in the cartridge of the present device, on the other hand, are tightly wound. If too much overgrowth has occurred and cells have begun to block certain sections of a cartridge, it is possible to simply increase the pressure across the device and "blow" the holes back open again to maintain the flow.

Alternate configurations can be used with a device of the present invention. One can change the size of the device, as well as varying the pitch on the windings and obtain various packing configurations, having more or less open space depending on how much open space is desired beyond the surface area of the fibers.

In a preferred embodiment, the cartridge of the invention can be equipped with secondary fibers. During the winding process in which the cartridge is formed, one may deposit secondary fibers along the axis at any frequency so that the secondary fibers are directed along the length of the cartridge parallel to the central spindle while the rest of the fibers encircle the spindle and envelope the parallel fibers. One advantage of using secondary fibers is that these can be hollow. This allows the device to be embedded with a flow system of hollow fibers that can either be looped back to both ends or can be continuous throughout the cartridge, and can be used to add nutrients or to remove specific materials. This can be done after closing the cartridge so that there is no external flow.

Having now generally described this invention, the same will become better understood by reference to certain specific examples which are included for purposes of illustration only and are not intended to be limiting unless otherwise specified.

EXAMPLE 1

Fiber Experiments with SC-1 Cells

Materials and Methods

Five different fibers were studied to determine if the fibers were a suitable substrate for cell attachment and growth. The following fibers were tested:
1. Polystyrene fibers spun from a Corning tissue culture flask
2. Polypropylene 6 mil
3. Elastane ® A879-11-1 HS (Resin 816 343-4)
4. Polyester (Dupont Dacron ®) 1100/192
5. Nylon 6 (Allied) 100/32.

The fibers were cut into 40–50 mm lengths and soaked in absolute alcohol for one hour. In some experiments, fibers which had not been soaked in alcohol were also tested.

A continuous line of mouse embryo fibroblasts, SC-1 cells, originally obtained from the American Type Culture Collection was used in this study. The cells were grown in 60-mm plastic tissue culture dishes (Falcon) and in untreated plastic Petri dishes. The SC-1 cells were grown in Eagle's Minimum Essential Medium (MEM) (GIBCO) supplemented with 5% heat-inactivated fetal bovine serum (Sterile Systems), 100 $\mu$g/mL streptomycin (Lilly), and 100 units/mL penicillin (Lilly).

An inoculum of $3.5 \times 10^5$ cells in 5 mL of appropriate medium was added to the culture dish containing the fibers to be tested. The SC-1 cells formed a confluent monolayer on a solid substrate.

The trypan blue-dye-exclusion procedure was used to determine the viability of the cells which attached to the test fibers. This dye is excluded from living cells, but is incorporated into dead cells.

Results

SC-1 cells in tissue culture dishes were used for the initial experiment to determine which of the fibers could be used as a substrate for cell growth. Of the five fibers tested, the polystyrene fibers spun from the Corning tissue culture flask exhibited the greatest affinity for the cells. However, the cells had a definite preference for growth on the surface of the tissue culture dish rather than on the surface of the fibers. A few cells attached to the length of the fibers, but the heaviest area of the cell attachment was at the ends of the fibers which had been cut with metal scissors. Even though the cells showed no preference for growing on the fibers, the fibers did not appear to be toxic to the cells as determined by the trypan blue dye-exclusion test. As a result of information obtained from this experiment, all subsequent work was done using the polystyrene fibers, in both tissue culture and petri dishes.

In an attempt to improve cell adhesion, the polystyrene fibers were seeded into tissue culture and petri dishes containing the treated fibers. The cells grew in a confluent monolayer on the surface of the fibers and the surface of the tissue culture dishes. Only a few cells attached to the surface of the petri dishes, but the cells formed a confluent monolayer on the surface of the fibers in the petri dishes. Large agglomerates of cells were attached to the fibers in some areas in the petri dishes. On Day 4, a fiber was removed from each culture, the cells were stained with aceto-orcein, and photomicrographs were made. No difference in cell attachment and growth was observed between the fibers which had or had not been soaked in alcohol.

After an initial experiment indicated that a glow discharge treatment to the polystyrene would increase the attachment of the SC-1 cells to the fibers, three different methods of applying the treatment were used. The following samples were prepared:

1. Polystyrene fibers 10 mA, 250 v direct current charge applied in an atmosphere of oxygen for about 5 minutes.
2. Polypropylene fibers 10 mA, 250 v direct current charge applied in an atmosphere of ammonia for about 5 minutes.
3. Elastane fibers 10 mA, 250 v direct current charge applied in an atmosphere of argon for about 10 minutes.

The SC-1 cells grew well on all of the fibers, but cell growth on the fibers charged in the presence of oxygen or ammonia was slightly better than the growth of the cells on the fibers charged in the presence of argon.

Some of the untreated polystyrene fibers were then coated with 0.1% collagen in deionized water or 0.5% poly-L-lysine in deionized water. The fibers were soaked for 2 h in the solution, washed for 10 minutes in deionixed water, and spread on absorbent paper towels to dry overnight. The fibers were then prepared for use in the experiment as previously described. In the petri dishes, the SC-1 cells grew on both the collagen and poly-L-lysine coated fibers. In the tissue culture dishes, only the poly-L-lysine coated fibers which were not washed with alcohol supported growth of the cells. The growth of the SC-1 cells on either of these coated fibers did not appear to be as heavy or as evenly distributed as had been observed on fibers which had an electrical charge applied.

Polystyrene fibers were then exposed to a glow discharge (10 mA, direct current in an argon atmosphere) for time intervals of 1, 5, 15, and 30 seconds and 1 and 5 minutes. SC-1 cells were then added to tissue culture and petri dishes containing these charged fibers and control fibers to which no treatment was applied. After 2 days incubation the control fibers had only a few cells attached to the cut ends of the fibers. The fibers which had been exposed to the glow discharge for 1, 5, or 15 seconds had heavy cell growth on the fibers. Cell attachment and growth on the fibers exposed to the glow discharge for 30 s, 1, and 5 minutes was very uneven. Some areas of the fibers exposed for 1 or 5 minutes appeared to be toxic to the cells.

The polystyrene fibers were next exposed to the corona discharge from a portable vacuum leak detector. The fibers were placed in petri dishes and the corona discharge applied to the fibers in the dish. SC-1 cells were added to the same dishes which had been used for exposing the fibers to the glow discharge. The process of treating the fibers also treated the surface of the petri dish and as a result, the cells attached to the surface of the dish as well as the surface of the fibers. This experiment was repeated with the following changes made in the procedure: The fibers were placed in aluminum weighing pans for exposure to the glow discharge. One group of fibers was exposed for about 1 second, the fibers were turned over with forceps, and the glow discharge applied for an additional second. The fibers were then transferred to a petri dish. The procedure was repeated with another group of fibers in an aluminum pan. This group of fibers was exposed to the glow discharge for a longer period of time (approximately 5 to 10 seconds). Only a few SC-1 cells attached to the untreated control fibers. The charged fibers had areas of heavy and light cell growth, but no fibers were observed to have a completely confluent monolayer of cells after two days.

EXAMPLE 2

Fiber Experiments with KB Cell Culture

The purpose of this experiment was to determine if KB cells in culture would grow and proliferate on synthetic fibers.

Materials

KB Cell Culture: a human epidermoid carcinoma of the nasopharynx initiated into cell culture by Dr. Harry Eagle, 1954 (Eagle, H. Proc. Soc. Exptl. Biol. Med. 89: 362, 1955).

Growth Medium

Eagle's Basal Medium supplemented with 10% calf serum (Flow Laboratories, McLean, Va.) (Eagle, H. J. Exptl. Med. 102: 595, 1955). Plastic tissue culture dishes, 60×15 mm (Falcon-Becton Dickinson Labware, Oxnard, Calif.)

Fibers (1) polystyrene (from Corning Tissue Culture Flasks)
(2) polypropylene-6 mil
(3) Elastane ® A879-11-1-1HS
(4) Polyester 1100/192 Dupont Dacron ®
(5) Nylon 6 100/32

Methods

Fibers were cut to approximately 50 mm lengths and soaked in absolute alcohol for 1 hour. Fibers were placed at random in 60×15 mm plastic tissue culture dishes (1 fiber type per dish). KB cells suspended in growth medium at 200,000 cells/mL were added to each test dish in a 5 mL volume (total $1 \times 10^6$ cells per dish). One cell control dish (without fibers) was included with each test. The dishes were incubated for 24 and 48 hours in 5% $CO_2$ and air at 37° C. The dishes were examined under an inverted microscope for cell proliferation and attachment to fibers.

Test Results (1) Five different types of fibers incubated in the presence of KB cells: No cell attachment seen.

(2) Polystyrene electrically charged fibers, alcohol and non-alcohol treated, plus KB cells: Few cells attached to the ends of fibers.

(3) Polystyrene fibers charged with $O_2$, $NH_4$, and argon plus KB cells: Cells attached to ends of fibers in all three conditions; Cells attached sparsely along fibers charged with argon.

(4) Polystyrene fibers without alcohol treatment coated with poly-lysine and collagen (separately), plus KB cells: Cells attached to fibers with collagen coating. No cell attachment seen on poly-lysine coated fibers.

Conclusions

The fibers used will vary in their ability to promote attachment of cells, depending on the type of fiber, of cell and of fiber treatment prior to attachment. However, conditions for the growth and attachment of any cell can routinely be found with only minor experimentation, and allows application of the methods to an unlimited number of fibers and cells. Placement of the chosen fibers and cells inside a cartridge device of the invention yields an efficient and stable system for the large scale cultivation of such cells.

Having now fully described this invention, it will be understood by those skilled in the art that the same can be carried out within a wide and equivalent range of compositions, cells, methodologies, fibers, windings, sizes, and the like without effecting the spirit or scope of the invention or any embodiment therein.

What is claimed as new and desired to be secured by Letters Patent of the United States is:

1. A method of cultivating cells in vitro which comprises:
    culturing cells selected from the group consisting of cells of animal, vegetable, microbiological and artificial origin in a cell culture device comprising an elongated housing of impermeable material, closed at its ends by means of impermeable end plates, said housing on its interior having a plurality of axial ribs extending substantially throughout the length thereof, an inlet port in one of said end plates, an outlet port in the other end of said end plates, said ribs continuing radially in said other of said end plates, an impermeable spindle axially disposed in said housing and having axially disposed grooves in its periphery, a cylindrical port secured to one end of said spindle and in communication with said inlet port and with said grooves, said spindle at its other end terminating in a conical tip axially disposed with respect to said outlet port with an annular space therebetween, and a spool of fiber helically wound on said spindle to substantially fill the interior of said housing into said ribs, whereby fluid entering said inlet port flows along said spindle grooves, passes through said fibrous spool, flows alongside said housing between said ribs, and then between said conical tip and said outlet port, said fiber having attached thereon the cells.

2. In a method of obtaining a substance which originates in cells of animal, plant, microbiological or artifical origin, comprising:
    (a) cultivating cells selected from the group consisting of cells of animal, vegetable, microbiological or artificial origin in vitro while maintaining said cells immobilized, and
    (b) thereafter collecting said products from said cells;
    wherein the improvement comprises
    said cells are immobilized in a cell culturing device comprising an elongated housing of impermeable material, closed at its ends by means of impermeable end plates, said housing on its interior having a plurality of axial ribs extending substantially throughout the length thereof, an inlet port in one of said end plates, an outlet port in the other end of said end plates, said ribs continuing radially in said other of said end plates, an impermeable spindle axially disposed in said housing and having axially disposed grooves in its periphery, a cylindrical port secured to one end of said spindle and in communication with said inlet port and with said grooves, said spindle at its other end terminating in a conical tip axially disposed with respect to said outlet port with an annular space therebetween, and a spool of fiber helically wound on said spindle to substantially fill the interior of said housing into said ribs, whereby fluid entering said inlet port flows along said spindle grooves, passes through said fibrous spool, flows alongside said housing between said ribs, and then between said conical tip and said outlet port, said fiber having attached thereon the cells.

3. The method of claim 1 wherein the cells are virus producing cells.

4. The method of claim 1 wherein the cells are of animal origin.

5. The method of claim 4 wherein the cells are of mammalian origin.

6. The method of claim 1 wherein the cells are hybridomas.

7. The method of claim 1 wherein the cells are directly immobilized on the fibers.

8. The method of claim 1 wherein the cells are immobilized on said fibers by means of chemical anchoring compounds selected from the group consisting of poly-lysine and collagen.

9. The method of claim 1 wherein the fiber is an electrically charged fiber.

10. The method of claim 9 wherein the fiber was electrically charged by glow discharge or corona discharge.

11. The method of claim 1 wherein the fiber was charged with a gas selected from the group consisting of $O_2$, $NH_4$ and argon.

12. The method of claim 2 wherein the cells are virus producing cells.

13. The method of claim 2 wherein the cells are of animal origin.

14. The method of claim 13 wherein the cells are of mammalian origin.

15. The method of claim 2 wherein the cells are hybridomas.

16. The method of claim 2 wherein the cells are directly immobilized on said fibers.

17. The method of claim 2 wherein the cells are immobilized on the fibers by means of chemical anchoring compounds selected from the group consisting of poly-lysine and collagen.

18. The method of claim 2 wherein the fiber is an electrically charged fiber.

19. The method of claim 18 wherein the fiber was electrically charged by glow discharge or corona discharge.

20. The method of claim 2 wherein the fiber was charged with a gas selected from the group consisting of $O_2$, $NH_4$ and argon.

* * * * *